(12) United States Patent
Fujita et al.

(10) Patent No.: US 7,769,565 B2
(45) Date of Patent: Aug. 3, 2010

(54) SAMPLE MEASUREMENT DEVICE, MEASUREMENT INFORMATION DISPLAY METHOD, AND COMPUTER SYSTEM

(75) Inventors: Kyozo Fujita, Hamburg (DE); Hiroyuki Fujino, Kakogawa (JP); Yoshihiro Mishima, Kobe (JP)

(73) Assignee: Sysmex Corporation, Kobe (JP)

( * ) Notice: Subject to any disclaimer, the term of this patent is extended or adjusted under 35 U.S.C. 154(b) by 67 days.

(21) Appl. No.: 11/895,449

(22) Filed: Aug. 24, 2007

(65) Prior Publication Data

US 2008/0071503 A1 Mar. 20, 2008

(30) Foreign Application Priority Data

Aug. 25, 2006 (JP) ............................. 2006-229914

(51) Int. Cl.
*G06F 19/00* (2006.01)
*G06F 17/40* (2006.01)

(52) U.S. Cl. ................... 702/190; 702/187; 702/189; 707/602; 715/273; 715/771

(58) Field of Classification Search ............... 702/189, 702/190, 1, 127, 179, 180, 181, 182, 187; 700/90, 95, 97, 98, 108; 707/1, 3, 4, 10, 707/101, 104.1, 200, 201, 600, 602; 715/200, 715/212, 221, 222, 224, 227, 273, 700, 764, 715/765, 771, 866
See application file for complete search history.

(56) References Cited

U.S. PATENT DOCUMENTS

| | | | |
|---|---|---|---|
| 6,391,263 B1 * | 5/2002 | Mishima et al. ............... | 422/67 |
| 6,853,389 B1 * | 2/2005 | Ikeda ........................ | 715/790 |
| 6,879,867 B2 * | 4/2005 | Tanaka et al. ............... | 700/108 |
| 7,058,467 B2 * | 6/2006 | Tanaka et al. ............... | 700/108 |
| 7,571,191 B2 * | 8/2009 | Dill et al. .................... | 707/200 |
| 2002/0087515 A1 * | 7/2002 | Swannack et al. ............. | 707/2 |
| 2004/0267751 A1 * | 12/2004 | Dill et al. ..................... | 707/9 |
| 2005/0027683 A1 * | 2/2005 | Dill et al. ..................... | 707/2 |
| 2006/0004745 A1 * | 1/2006 | Kuhn et al. ................... | 707/4 |
| 2006/0190187 A1 * | 8/2006 | Mishima et al. ............... | 702/19 |
| 2006/0235741 A1 * | 10/2006 | Deaton et al. ................. | 705/10 |
| 2006/0247866 A1 * | 11/2006 | Mishima et al. ............... | 702/19 |
| 2006/0259265 A1 * | 11/2006 | Mishima et al. ............. | 702/118 |
| 2006/0263905 A1 * | 11/2006 | Mishima et al. ............. | 436/520 |

(Continued)

FOREIGN PATENT DOCUMENTS

EP 1 033 573 A2 * 9/2000

(Continued)

*Primary Examiner*—Edward R Cosimano
(74) *Attorney, Agent, or Firm*—Brinks Hofer Gilson & Lione

(57) ABSTRACT

A measurement information display method includes: generating measurement information of a sample according to progress of measurement of the sample by a measurement unit for measuring the sample, and accumulating the measurement information in a storage part, the measurement information including state information indicating a state of the measurement by the measurement unit; accepting extracting information including an extracting condition regarding the state of measurement of the sample used in extracting the accumulated measurement information, and storing the extracting information in a memory; accepting a selection of the extracting information stored in the memory; extracting the measurement information from the accumulated measurement information according to the selected extracting information; and displaying the extracted measurement information.

16 Claims, 15 Drawing Sheets

U.S. PATENT DOCUMENTS

2006/0265173 A1* 11/2006 Mishima et al. ............. 702/118
2008/0011106 A1* 1/2008 Kitagawa et al. .............. 73/863
2008/0014118 A1* 1/2008 Kitagawa et al. .............. 422/64
2008/0050279 A1* 2/2008 Fujita .......................... 422/67
2008/0050280 A1* 2/2008 Fujita .......................... 422/67
2008/0063570 A1* 3/2008 Fujino et al. ................. 422/99
2008/0183431 A1* 7/2008 Matsuo et al. .............. 702/187
2009/0259408 A1* 10/2009 Mishima et al. ............... 702/19

FOREIGN PATENT DOCUMENTS

JP 07-159412 6/1995

* cited by examiner

FIG.12

SAMPLE MEASUREMENT DEVICE, MEASUREMENT INFORMATION DISPLAY METHOD, AND COMPUTER SYSTEM

RELATED APPLICATIONS

This application claims priority under 35 U.S.C. §119 to Japanese Patent Application No. 2006-229914 filed Aug. 25, 2006, the entire content of which is hereby incorporated by reference.

FIELD OF THE INVENTION

The present invention relates to a sample measurement device, a measurement information display method, and a computer system.

BACKGROUND

The display technique of an analyzer is disclosed in Japanese Laid-Open Patent Publication No. H7-159412 and the like. In the analyzer of Japanese Laid-Open Patent Publication No. H7-159412, a search condition setting screen for setting the conditions characterizing the sample is arranged, where a search condition button is selected with a keyboard in the search condition setting screen to select the necessary conditions, and a set button is thereafter selected to complete the input of conditions in the analyzer in order to display the result of analysis corresponding to the conditions set in the screen.

In the analyzer disclosed in Japanese Laid-Open Patent Publication No. H7-159412, the search conditions must be input every time the user searches for the measurement result. The user often repeatedly performs the search with the same search conditions due to operation etc. of the measurement result management of a facility. In the technique described in Japanese Laid-Open Patent Publication No. H7-159412, the user must repeatedly input the same search conditions in a case of complex search conditions, which tends to be very troublesome.

BRIEF SUMMARY

The scope of the present invention is defined solely by the appended claims, and is not affected to any degree by the statements within this summary.

The first aspect of the present invention relates to a sample measurement device comprising:

a measurement unit for measuring a sample;

a storage part;

measurement information accumulating means for generating measurement information of the sample according to progress of measurement by the measurement unit and accumulating the generated measurement information in the storage part, the measurement information including state information indicating a state of the measurement by the measurement unit;

extracting information setting means for accepting extracting information including an extracting condition regarding the state of measurement of the sample used in extracting the accumulated measurement information, and storing the extracting information in the storage part;

selecting means for accepting a selection of the extracting information stored in the storage part;

extracting means for extracting the measurement information from the accumulated measurement information according to the extracting information selected by the selecting means; and a display section for displaying the measurement information extracted by the extracting means.

The second aspect of the present invention relates to a measurement information display method comprising steps of:

generating measurement information of a sample according to progress of measurement of the sample by a measurement unit for measuring the sample, and accumulating the measurement information in a storage part, the measurement information including state information indicating a state of the measurement by the measurement unit;

accepting extracting information including an extracting condition regarding the state of measurement of the sample used in extracting the accumulated measurement information, and storing the extracting information in a memory;

accepting a selection of the extracting information stored in the memory;

extracting the measurement information from the accumulated measurement information according to the selected extracting information; and displaying the extracted measurement information.

The third aspect of the present invention relates to a computer system adapted to display measurement information related to measurement of a sample, comprising:

a processor, a communication interface for communicating with a measurement unit for measuring the sample; and a memory, under control of said processor, including software instructions adapted to enable the computer system to perform operations comprising:

generating measurement information of the sample according to progress of measurement of the sample by the measurement unit, and accumulating the measurement information in the memory, the measurement information including state information indicating a state of the measurement by the measurement unit;

accepting extracting information including an extracting condition regarding the state of measurement of the sample used in extracting the accumulated measurement information, and storing the extracting information in the memory;

accepting a selection of the extracting information stored in the memory;

extracting the measurement information from the accumulated measurement information according to the selected extracting information; and displaying the extracted measurement information.

BRIEF DESCRIPTION OF THE DRAWINGS

FIG. 12 is a view showing a filter tab of the display condition dialogue when setting a new display condition;

DETAILED DESCRIPTION OF THE PREFERRED EMBODIMENTS

The embodiments embodying the present invention will now be described based on the drawings.

Figure 1:
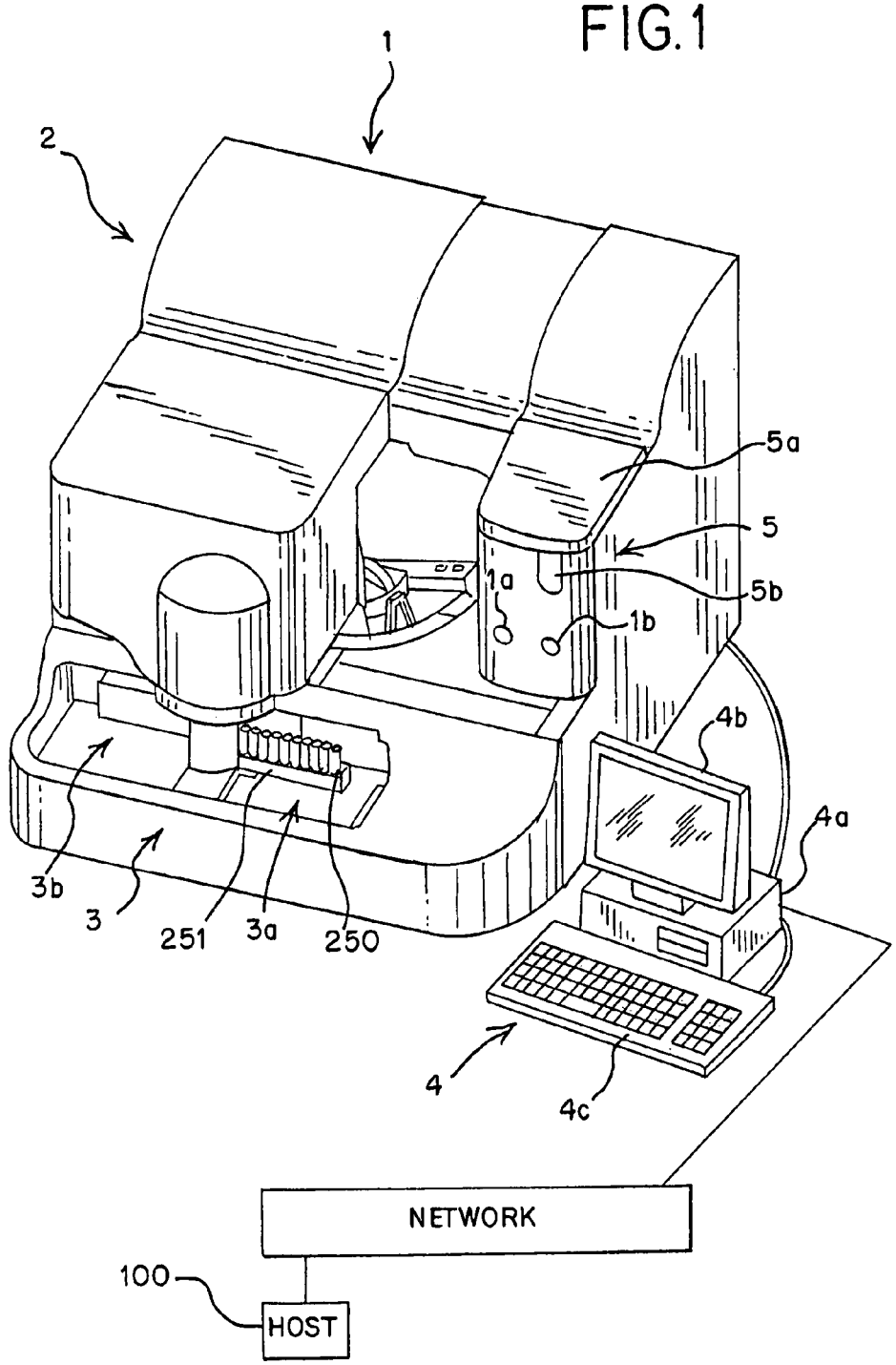
FIG. 1 is a perspective view of a sample measurement device.

A sample measurement device 1 shown in FIG. 1 is a device for optically measuring and analyzing the amount and extent of activity of a specific substance related to coagulation and fibrinolytic functions of the blood, where plasma is used for the specimen (sample). In the sample measurement device 1, optical measurement of the specimen is performed for a plurality of measurement items using coagulation time method, synthetic substrate method, and immunoturbidimetric method.

The coagulation time method used in the present embodiment is a measurement method of detecting the coagulating process of the specimen as change in transmitted light. The measurement items include PT (prothrombin time), APTT (activated partial thromboplastin time), Fbg (Fibrinogen content), and the like. The measurement items of the synthetic substrate method include ATIII etc., and the measurement items of the immunoturbidimetric method include D dimer, FDP etc.

The sample measurement apparatus 1 is configured by a measurement mechanism unit 2, and a control device 4 electrically connected to the measurement mechanism unit 2. A specimen conveying mechanism unit 3 is arranged on the front face side of the measurement mechanism unit 2.

The specimen conveying mechanism unit 3 has a function of conveying a rack 251 mounted with a plurality of test tubes 250 accommodating the specimen to a suction position of the measurement mechanism unit 2 to supply the specimen to the measurement mechanism unit 2. The specimen conveying mechanism unit 3 includes a rack set region 3a for setting the rack 251 stored with the test tubes 250 accommodating the non-processed specimen, and a rack accommodating region 3b for setting the rack 251 stored with the test tubes 250 accommodating the processed specimen.

The measurement mechanism unit 2 is configured to acquire the optical information on the supplied specimen by performing an optical measurement on the specimen supplied from the conveying mechanism unit 3. In the present embodiment, the optical measurement is performed on the specimen dispensed into a cuvette of the measurement mechanism unit 2 from the test tube 250 mounted on the rack 251 of the conveying mechanism unit 3.

The measurement mechanism unit 2 is arranged with a cuvette placing section 5 for supplying the cuvette to which the specimen of when performing the measurement is dispensed. The cuvette placing section 5 includes an openable/closable lid 5a, and a window 5b enabling the inside of the cuvette placing section 5 to be visible. The cuvette can be supplied to the cuvette placing section by opening the lid 5a from the closed state of FIG. 1. The user can visibly recognize the remaining amount of cuvettes in the cuvette placing section 5 from the window 5b.

An urgent stop button 1a and a measurement start button 1b are arranged on the front face side of the cuvette placing section 5. The urgent stop button 1a is provided to stop the measurement in time of urgency. The measurement start button 1b is adapted to start the measurement of the specimen when pushed. The user thus can immediately start the measurement after placing the cuvette. The measurement can also be started or stopped through operation of the control device 4.

The measurement mechanism unit 2 includes an operation control section (not shown), and controls the measurement operation and the conveying operation of the measurement mechanism unit 2 and the specimen conveying mechanism unit 3.

Figure 2:
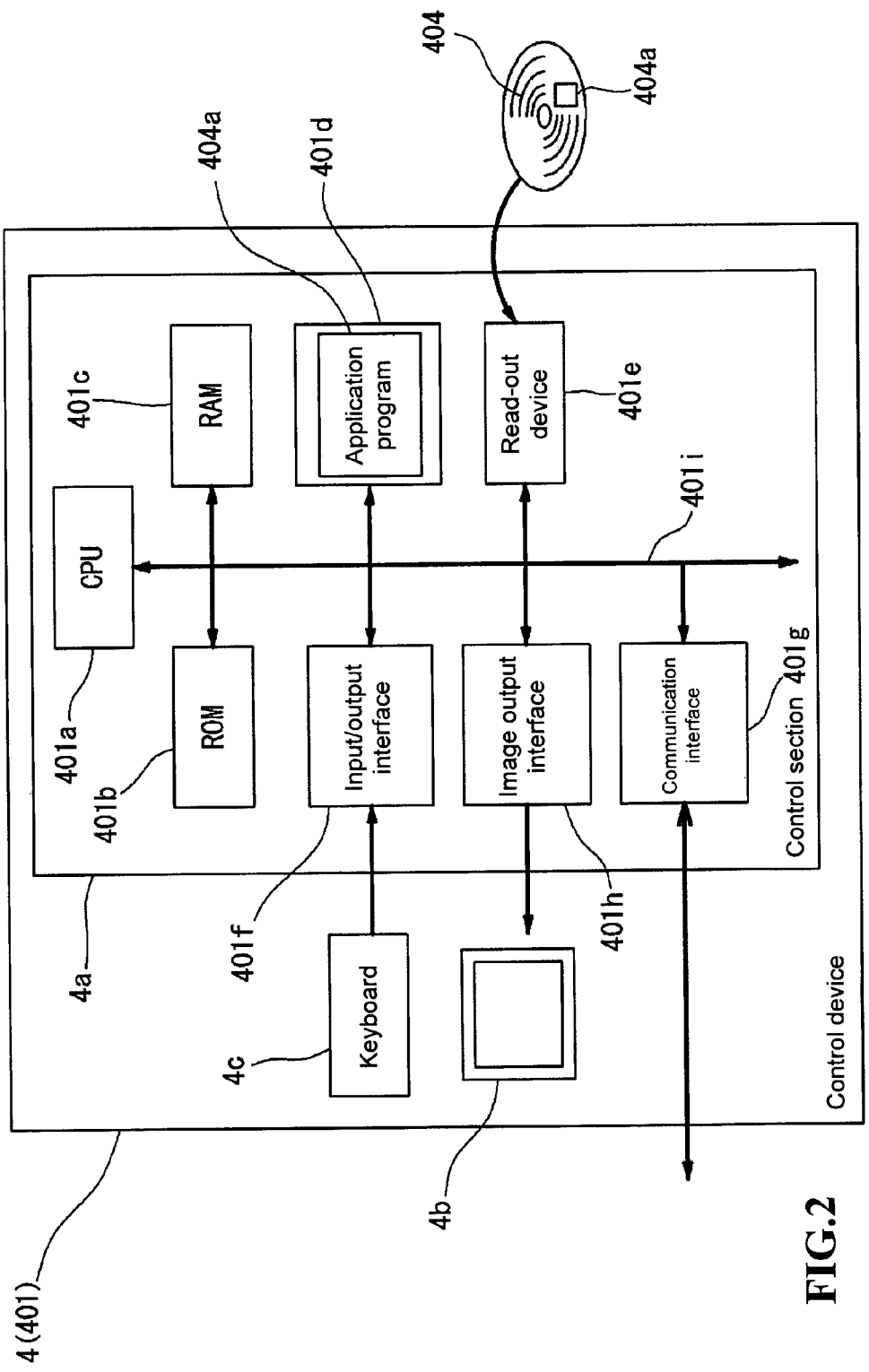
FIG. 2 is a hardware construction view of a control section of the sample measurement device.

The control device 4 consists of personal computer (PC) 401, and includes a control section 4a, a display device 4b, and an input section 4c such as keyboard, as shown in FIGS. 1 and 2.

The control section 4a is connected to an operation control section of the measurement mechanism unit 2, and is able to transmit an operation command to the operation control section. The control section 4a can also receive and accumulate the measurement information obtained in the measurement mechanism unit 2, and analyze the measurement information.

As shown in FIG. 2, the control section 4a is mainly configured by a CPU 401a, a ROM 401b, a RAM 401c, a hard disc 401d, a read-out device 401e, an input/output interface 401f, a communication interface 401g, and an image output interface 401h, which are connected by a bus 401i.

The CPU 401a executes computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The application program 404a for realizing the function of the control section 4a related to extraction and display of the measurement information as well as other functions of the control section 4a, to be hereinafter described, in the present embodiment are also installed in the hard disc 401d.

The read-out device 401e is configured by flexible disc drive, CD drive, DVD drive, and the like, and is able to read out computer programs and data recorded on a portable recording medium 404. The application program 404a in the present embodiment is stored in the portable recording medium 404, where the computer 401 can read out the application program 404a from the portable recording medium 404, and install the application program 404a in the hard disc 401d.

The application program 404a is not only provided by the portable recording medium 404, but also provided through communication line (wired or wireless) from external devices communicatably connected with the computer 401 by the communication line. For instance, the application program 404a may be stored in the hard disc of the server computer on the Internet, where the computer 401 can access the server computer to download the application program 404a and install the application program 404a in the hard disc 401d.

Operating system providing graphical user interface environment such as Windows (registered trademark) manufactured and sold by US Microsoft Co. is installed in the hard disc 401d. In the following description, the application program 404a according to the present embodiment is assumed to be operating on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 transmits and receives data with the measurement mechanism unit 2 using a predetermined communication protocol by means of the communication interface 401g. The computer 401 can also communicate with other computers such as host computer 100 via a network such as LAN by the communication interface 401g.

The image output interface 401h is connected to the display device 4b configured by LCD, CRT, or the like, and is configured to output the image signal corresponding to the image data provided from the CPU 401a to the display section 4b. The display device 4b displays the image (screen) according to the input image signal. The display device 4b has a touch panel function, so that the button or the icon displayed on the display screen can be selected or operated by being directly touched by the user.

Figure 3:
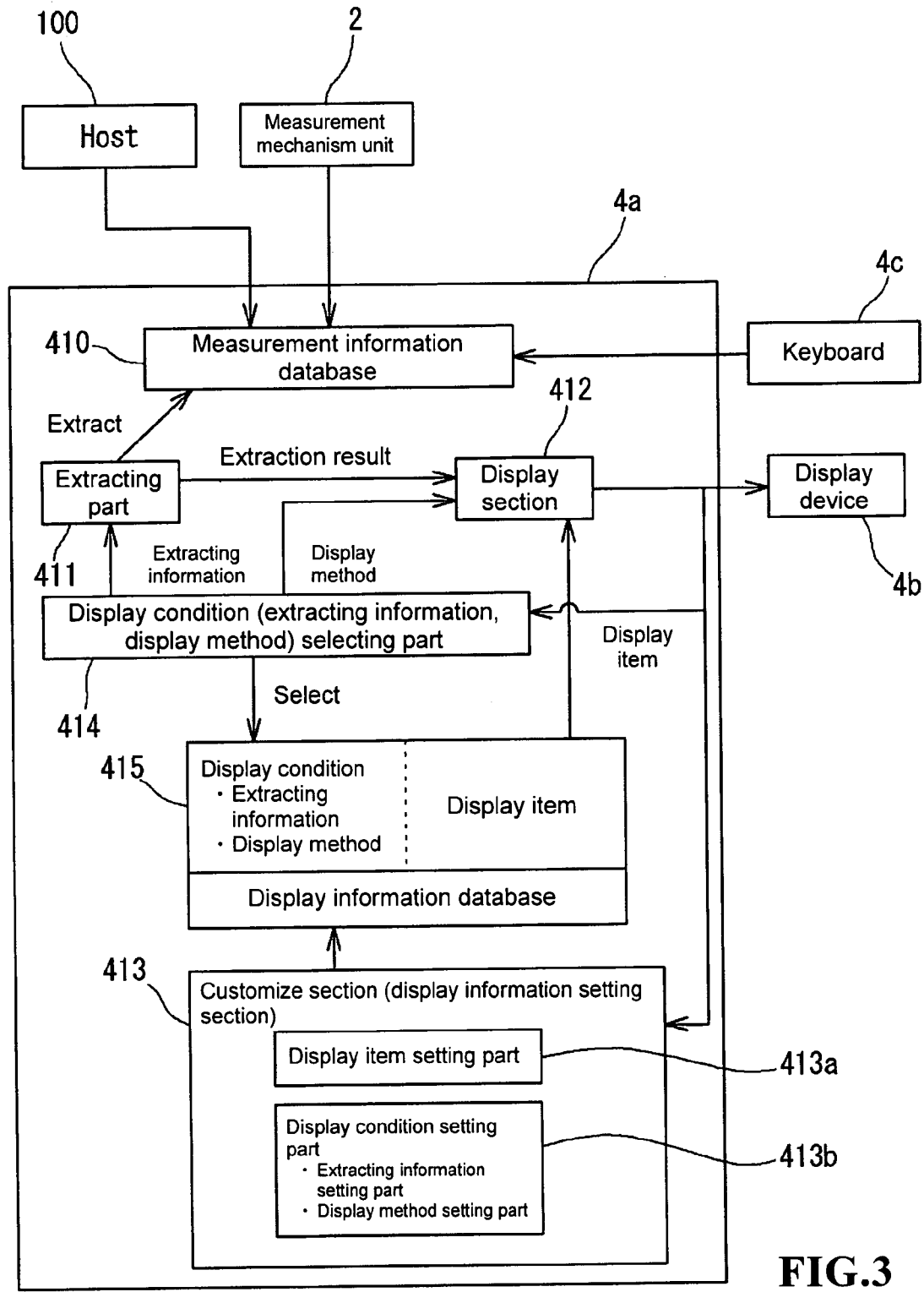
FIG. 3 is a functional block diagram of the control section of the sample measurement device.

FIG. 3 is a block diagram showing the functions related to the display of the measurement information of the control section 4a realized by the application program. As shown in FIG. 3, the control section 4a includes a measurement information database 410, an extracting part 411 for extracting the measurement information from the measurement information database, a display part 412 for displaying the extracted measurement information on the display device 4b, a customize section 413 for setting the display information, a display condition selecting part 414 for the user to select the display condition, and a display information database registered with the display information. The details of each of such functions will be hereinafter described.

Figure 4:
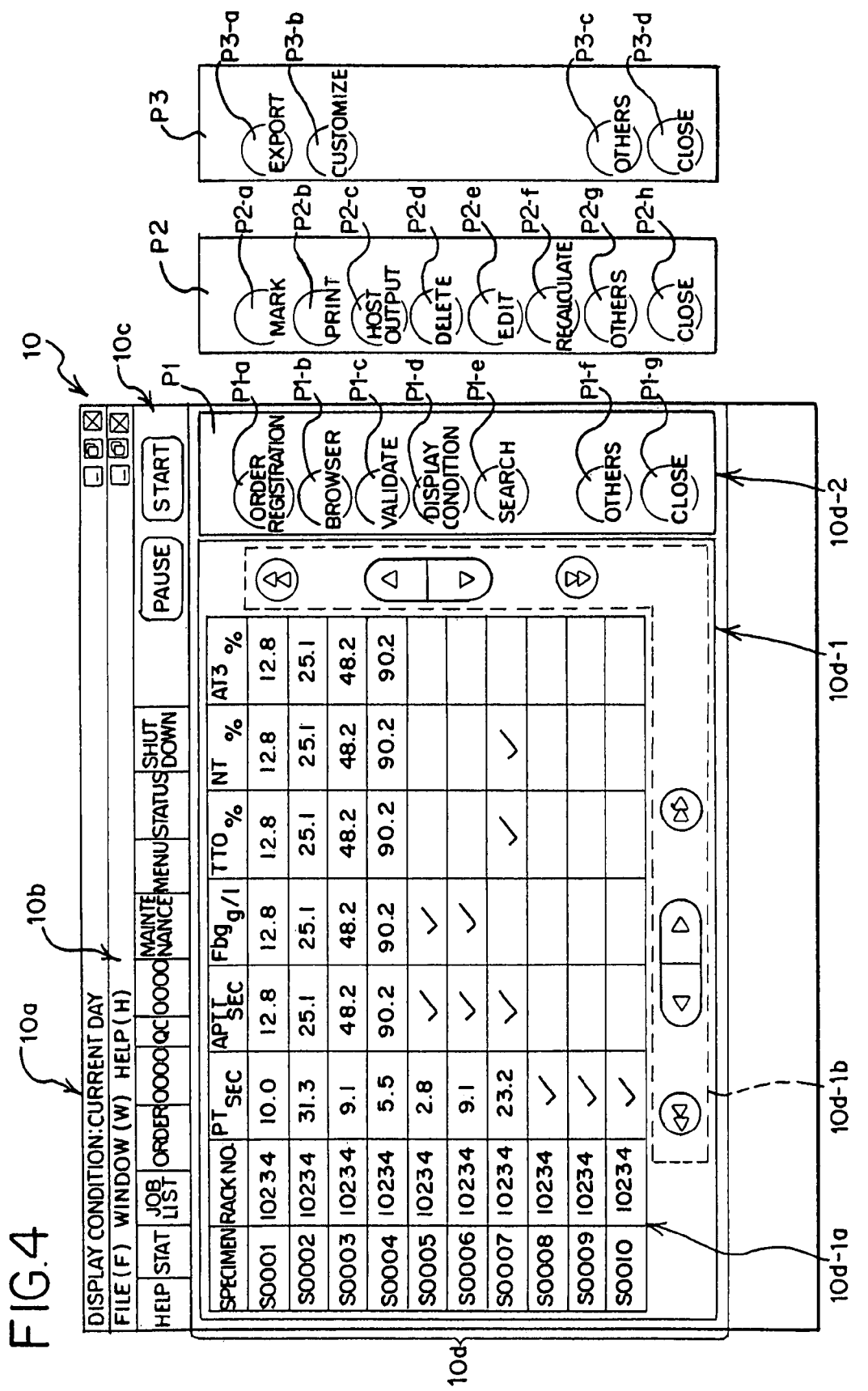
FIG. 4 is a view showing a display screen of the sample measurement device.

FIG. 4 shows a screen (window screen) 10 displayed on the display device 4b of control section 4 by the application program 404a. The screen 10 is provided to operate the measurement mechanism unit 2 and display the measurement information of the specimen.

The window screen 10 includes a title bar 10a for displaying the title of the window screen 10, a menu 10b of various functions that can be used in the application program 404a, a non-client region including a tool bar 10c for selecting the various functions that can be used in the application program 404a, and a client region 10d at where various displays are made.

[Regarding Measurement Information]

One measurement information displayed in a list part 10d-1a is generated for one measurement, where a plurality of data items is contained in one measurement information. A great number (e.g., 10000) of measurement information are accumulated in the measurement information database 410 of the control section 4a.

Figure 5:
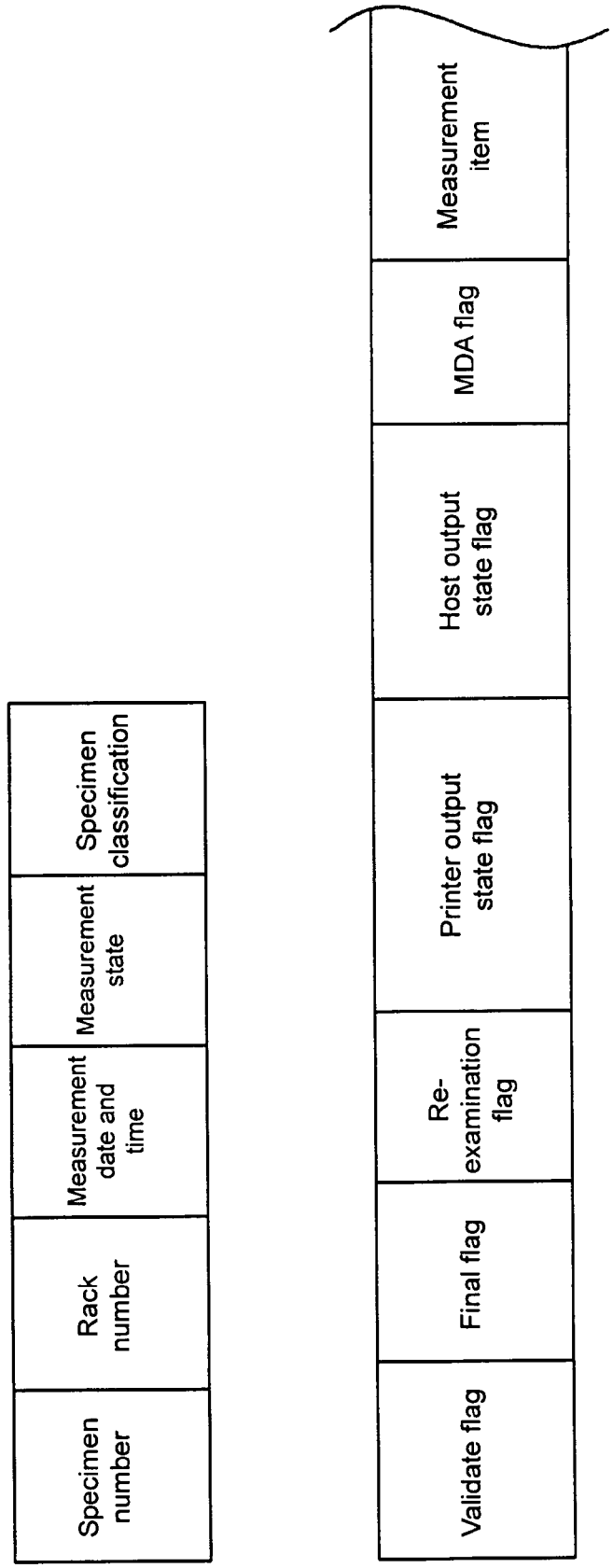
FIG. 5 is a view showing data items of the measurement information.

As shown in FIG. 5, the data items contained in one measurement information includes specimen number, rack number, measurement date and time, measurement state (non-measured, in-measurement, normal termination, termination requiring check, error termination), specimen classification (normal specimen, urgent specimen, analytical curve sample, precision management sample), validate flag, final flag, re-examination flag, printer output state flag, host output state flag, MDA flag, and various measurement items as well as other items.

The measurement information is generated when order registration of the measurement is performed, and each data item of the generated measurement information is generated or updated when order registration of the measurement is performed, when measurement is started, when measurement result of each measurement item is obtained, and when all the measurements are terminated.

For instance, in the order registration of the measurement, registration of specimen number scheduled to be measured, registration of specimen classification, and registration of measurement items to be measured for the relevant specimen out of the plurality of measurement items are performed, and furthermore, the measurement state is set and registered to "non-measured". When the measurement is started, the record of the measurement date and time are taken, and the measurement state is set and registered to "in-measurement".

After the measurement result of each measurement item is obtained, the measurement result is sequentially recorded for the corresponding measurement item in the measurement information. After all the measurements are terminated, the measurement state is set to one of "normal termination", "termination requiring check", or "error termination". The "normal termination" is when the measurement for all the measurement items is termination normally, the "termination requiring check" is when the measurement for all the measurement items is terminated but fault that needs to be checked by the user is found for one or more measurement items, and the "error termination" is when the measurement for all the measurement items is terminated but an error occurs for one or more measurement item.

Therefore, the measurement information includes, not only the measurement result of the specimen, but also the information related to the progress of the measurement as the data item of "measurement state". That is, a case in which the measurement is not terminated (non-measured or in-measurement) or a case in which the measurement is terminated (normal termination, termination requiring check, error termination) can be distinguished depending on the content of the "measurement state" data item of the measurement information. Furthermore, a case of "non-measured" in which the measurement has not started and a case of "in-measurement" in which the measurement has started can be distinguished for when the measurement is not terminated. The normal termination and abnormal termination (termination requiring check, error termination) can be distinguished for when the measurement is terminated.

Moreover, since the measurement information includes the data item "specimen classification", the type of specimen (sample) in each measurement information can be distinguished. Since the measurement information includes the data item "measurement date and time", the measurement date in each measurement information can be checked.

[Accumulation of Measurement Information]

Figure 14:
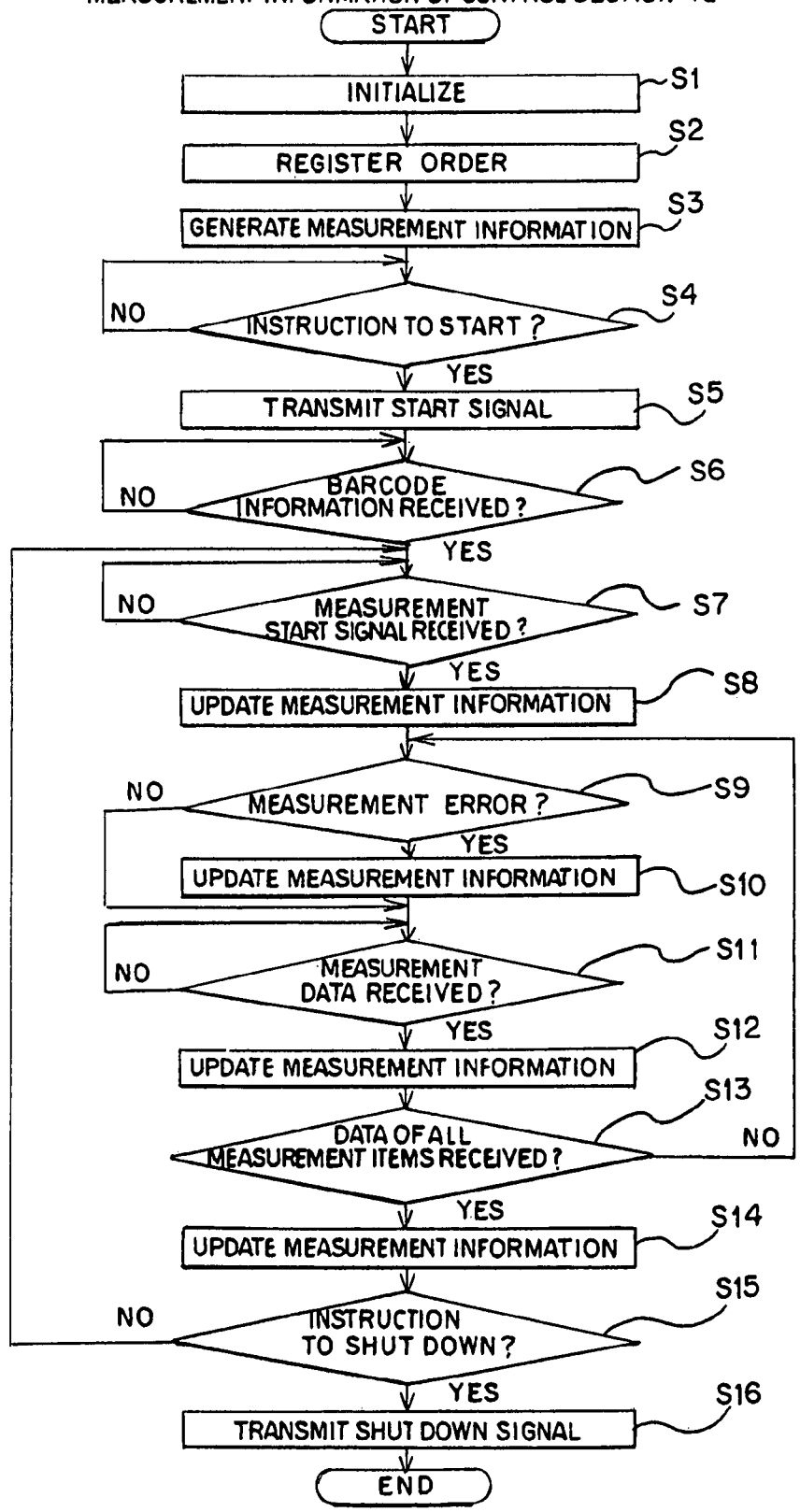
FIG. 14 is a flowchart of a generation /update process of the measurement information of the control section.

The operation of accumulating the measurement information by the sample measurement device 1 described above will now be described. FIG. 14 is a flowchart showing a generation/update process flow of the measurement information of the control section 4a. The generation/update process flow of the measurement information of the control section 4a will be described below with reference to FIGS. 1, 3, and 14.

When the power (not shown) of the control device 4 is turned ON by the user, initialization of the control section 4a (initialization of program) is performed in step S1, and at the same time, initialization of a control section (not shown) of the measurement mechanism unit 2 (initialization of program) and operation check of each section of the measurement mechanism unit 2 are performed, and the login process of the user is carried out. A menu screen (not shown), which is the initial screen to be hereinafter described, is displayed on the display device 4b of the control device 4.

Figure 13:
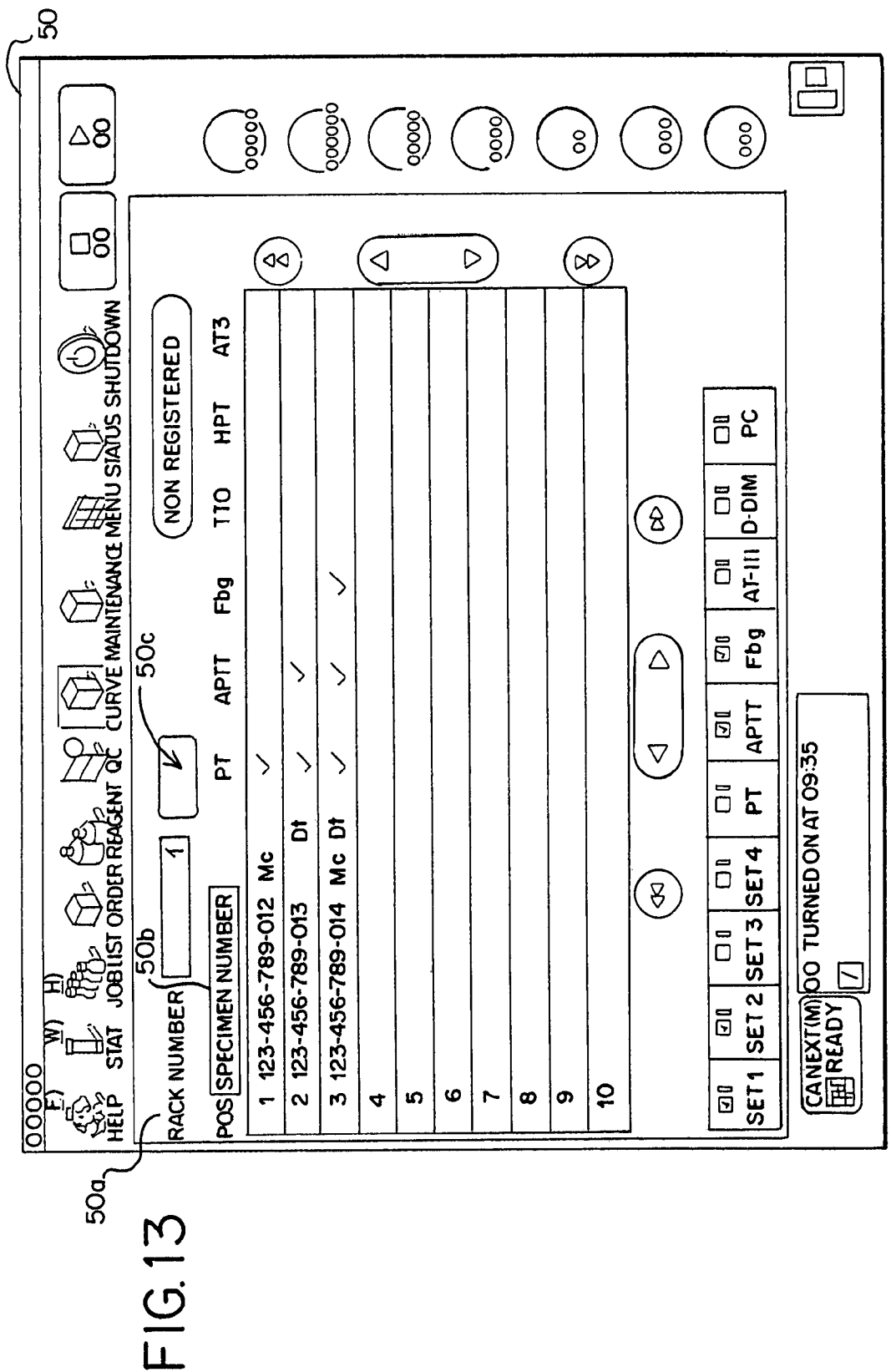
FIG. 13 is a view showing an order registration screen.

In step S2, the control section 4a accepts an order registration from the user. In the process of step S2, an icon for order registration provided on the menu screen is selected or an order registration button P1-a is selected from the operation panel region 10d-2 of a job list screen (see FIG. 4), whereby an order registration screen 50 shown in FIG. 13 is displayed and the order is registered by the user. Specifically, the user selects a rack number 50a, inputs a specimen number 50b, and selects a measurement item 50c on the order registration screen to register the order. After the order is registered, the measurement information including the information of the input rack number, the specimen number, and the measurement item are generated in step S3, and stored in the measurement information database 410 shown in FIG. 3. The non-measured flag is set in the measurement information stored in step S3.

When the user selects "start" button on the tool bar 10c of the screen 10 of FIG. 4 in step S4, a start signal is transmitted to the control section of the measurement mechanism unit 2 in step S5, and the measurement starts. The rack 251 mounted with a plurality of test tubes 250 accommodating the specimen is conveyed to the suction position of the measurement mechanism unit 2 by the specimen conveying mechanism unit 3 of the measurement mechanism unit 2 shown in FIG. 1, a barcode attached to the specimen is read, and the barcode information is transmitted to the control section 4a. If "start" is not selected, the process returns to step S4.

The barcode information is received by the control section 4a in step S6, and a measurement start signal corresponding to the measurement item is received from the control section of the measurement mechanism unit 2 in step S7. If barcode information is not received, the process returns to step S6. If the measurement start signal is not received, the process returns to step S7. In step S8, the flag of in-measurement corresponding to the relevant measurement item of the measurement information is set, and the measurement information of the measurement information database 410 is updated.

The control section 4a determines if there is measurement error in step S9, where if determined that there is measurement error, the flag of measurement error of the relevant measurement information is set, and the measurement information of the measurement information database 410 is updated in step S10. If determined that there is no measurement error in step S9, the process proceeds to step S11.

When the measurement data is received by the control section 4a in step S11, the in-measurement flag of the measurement information is canceled, the measurement data is written to the measurement result of the corresponding measurement item, and the measurement information of the measurement information database 410 is updated in step S12. If the measurement data is not received, the process returns to step S11.

The control section 4a determines whether or not the data of all the measurement items of the specimen are received in step S113, and if the data corresponding to all the measurement items of the specimen are received, the measurement completed flag of the relevant measurement information is set, and the measurement information of the measurement information database 410 is updated. If the data corresponding to all the measurement items of the specimen are not received in step S13, the process returns to step S9.

When the user selects shut down from the tool bar 10c (FIG. 4) of the screen 10 displayed on the display device 4b of the control device 4 by the user in step S15, a shut down signal is transmitted in step S16 to the control section of the control measurement unit 2 by the control section 4a, and the shut down process of the control device 4 and the measurement mechanism unit 2 is executed. If the shut down is not selected in step S15, the process returns to step S7.

[Extraction of Measurement Information]

Figure 15:
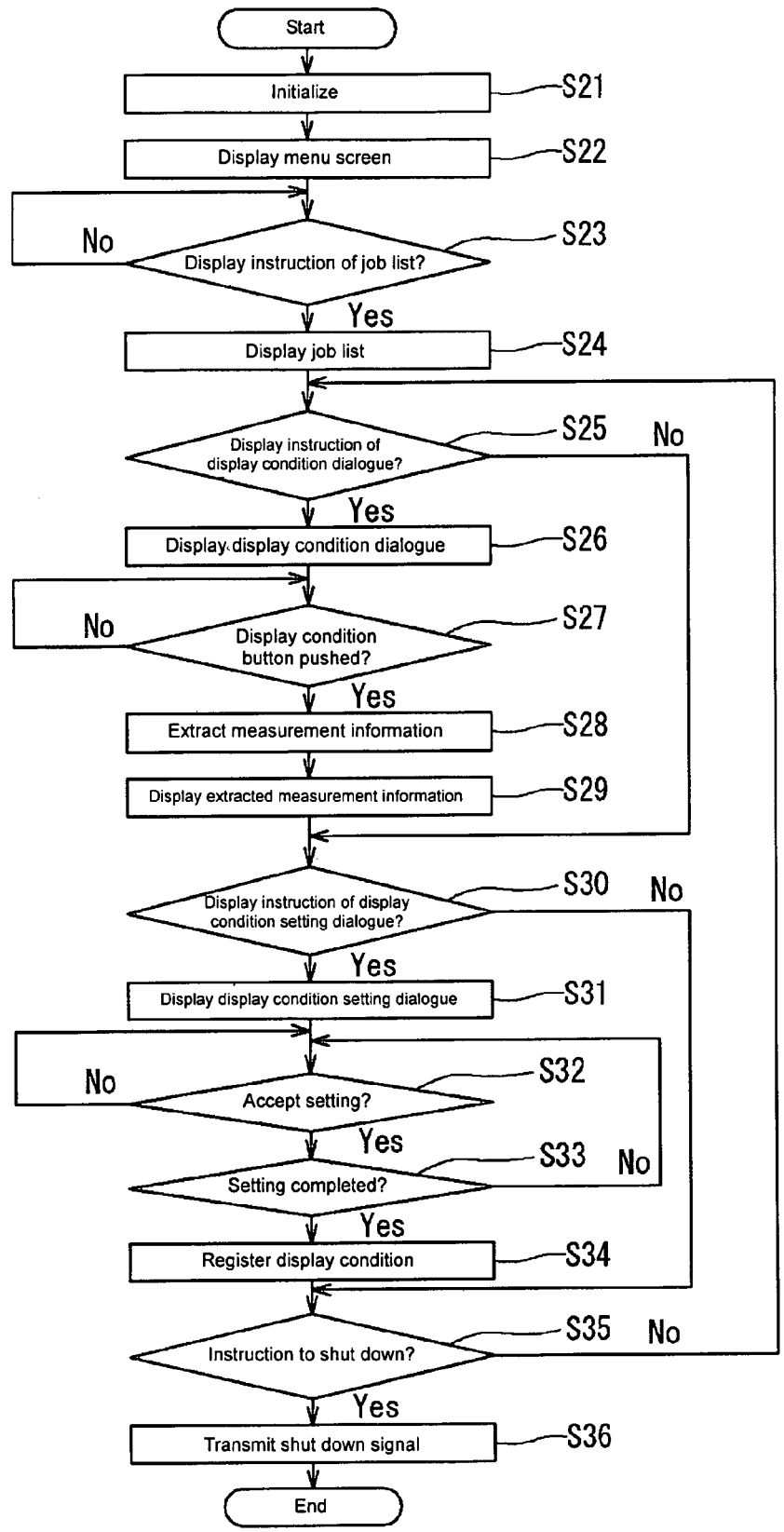
FIG. 15 is a flowchart of an extraction process of the measurement information of the control section.

The operation of the sample measurement device 1 to extract and display the measurement information accumulated in the measurement information database 410 in the above manner will now be described. FIG. 15 is a flowchart showing an extraction process flow of the measurement information of the control section 4a.

When the power (not shown) of the control device 4 is turned ON by the user, initialization of the control section 4a (initialization of program) is performed in step S21, and the menu screen (screen 10) which is the initial screen is displayed on the display device 4b of the control device 4 in step S22. In step S23, the display instruction of a job list is accepted by the user. The process of step S23 is performed by having the user select "Job list" in the tool bar 10c or "job list" (not shown) from the menu 10b shown in FIG. 4. When the display instruction of the job list is accepted from the user in step S23, the "job list" is displayed on the display device 4b in step S24. When the display instruction of the job list is not accepted by the user, the process returns to step S23. The screen 10 of FIG. 4 shows a state in which the "Job list" is selected, and the list of the measurement information is displayed in the client region 10d.

The display screen of the job list displayed in step S24 will be described in detail below. When the "Job list" is selected, the list display region 10d-1 and the operation panel region 10d-2 are displayed in the client region 10d. The list display region 10d-1 is provided to display, in a form of a list, the measurement information of the specimen and includes a list part 10d-1a and a button part 10d-1b. The list part 10d-1a is provided to display, in a form of a list, the measurement information in the measurement information database 410 accumulated in the storage part (hard disc 401d etc.) of the control section 4a. One measurement information displayed in one row in the list part 10d-1a, and a plurality of (ten herein) measurement information can be displayed all at once. The button part 10d-1b is provided to move the displayed list up and down, and left and right.

In addition to a first operation page P1 displayed on the screen 10, a second operation page P2 and a third operation page P3 are respectively displayed through page switching on the operation panel region 10d-2. Various operation buttons are displayed on each operation page P1 to P3.

An "order registration" button P1-a of the first operation page P1 is used to register the measurement order in the control section 4, where the measurement order registration screen is displayed by selecting the relevant button. A "browser" button P1-b separately displays the measurement result of the specimen, which is the cursor row in the list part 10d-1a, on the browser. A "validate" button P1-c is provided to validate the measurement result of the specimen, where the validate dialogue is displayed by selecting the relevant button.

A "display condition" button P1-d is provided to display a display condition selecting dialogue for selecting the conditions to display on the list part 10d-1a. A "search" button P1-e is provided to display a search dialogue to search for a specific specimen from a list displayed in the list part 10d-1a. An "others" button P1-f is provided to perform a switching operation to the next operation page P2. A "close" button P1-g is provided to close the job list screen and to return to the screen before the job list screen display.

A "mark" button P2-a of the second operation page is provided to mark each measurement information. A "print" button P2-b is provided to print the measurement information (measurement result), where a print dialogue is displayed by selecting the relevant button. A "host output" button P2-c is provided to output the measurement information (measurement result) to the host computer 100, where a host output dialogue is displayed by selecting the relevant button.

A "delete" button P2-d is provided to delete the measurement information of the specimen on which the measurement has been completed and the measurement information (order registration information) of the specimen on which the measurement is not performed, where a delete dialogue is displayed by selecting the relevant button. A "edit" button P2-e is provided to edit the measurement information (measurement result or order registration information), where an edit dialogue of the measurement result or the order registration information are displayed by selecting the relevant button, but a warning dialogue will be displayed if selected during the measurement.

A "recalculate" button P2-f is provided to recalculate the calculation items. An "others" button P2-g is provided to perform the switching operation to the next operation page P3. A "close" button P2-h is provided to close the job list screen and to return to the screen before the job list screen display.

An "export" button P3-a of the third operation page P3 is provided to export the measurement information in the measurement information database 410. A "customize" button P3-b is provided for the user to customize the display of the list part 10d-1a, where a customize dialogue is displayed by selecting the relevant button.

An "others" button P3-c is provided to perform the switching operation to the next operation page P1. A "close" button P3-d is provided to close the job list screen and to return to the screen before the job list screen display.

Figure 6:
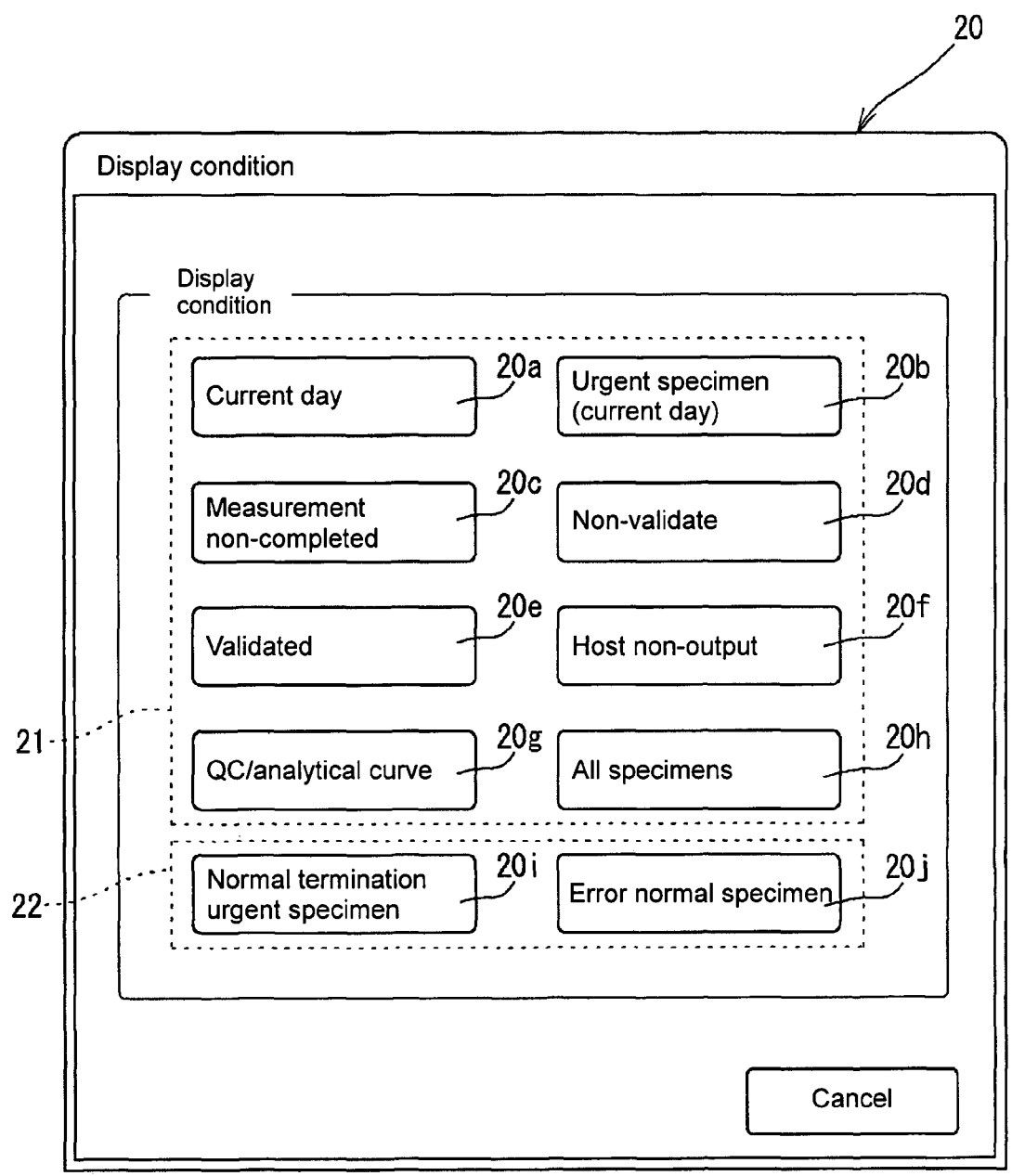
FIG. 6 is a view showing a display condition dialogue.

After such job list is displayed, whether or not the display instruction of the display condition dialogue is made is determined by the control section 4a in step S25 of the flowchart shown in FIG. 15. If the display instruction of the display condition dialogue is made in step S25, the display condition dialogue is displayed in step S26. Specifically, the user selects the "display condition" button P1-d to make the display instruction (see FIG. 4) of the display condition dialogue in step S25. The display condition dialogue (display condition selecting part 414, extracting information selecting means) 20 shown in FIG. 6 is then displayed (step S26). The buttons for selecting the display conditions already registered in the display information database 415 of the control section 4a are displayed the display condition dialogue 20 along with the names of the display conditions. Specifically, "current day" button 20a, "urgent specimen (current day)" button 20b, "measurement non-completed" button 20c, "non-validate" button 20d, "validated" button 20e, "host non-output" button 20f, "QC/analytical curve" button 20g, "all specimen" button 20f, "normal termination urgent specimen" button 20i, and "error normal specimen" button 20j are displayed. If the display instruction of the display condition dialogue is not made in step S25, the process proceeds to step S30.

Among such buttons, the "current day" button 20a to the "all specimen" button 20h are initial setting display conditions 21 already registered in the initial setting of the application program 404a, and the "normal termination urgent specimen" button 20i and the "error normal specimen" button 20j are customize display condition 22 set by the user. Since the initial setting display condition 21 is provided as the display condition, the user is able to use the basic display condition without requiring the user to purposely create the customize display condition. Since the customize display condition 22 can be provided, a flexible display condition according to the facility in which the sample measurement device 1 is installed can be set. The method of setting the customize display condition will be hereinafter described.

Each display condition 20a to 20j registered in the display information database 415 includes extracting information of the measurement information and information related to the method of displaying the extracted measurement information. The "extracting information" is a collection of one or a plurality of extracting conditions, where the extracting condition is the condition for extracting the measurement information to display from a great number of measurement information accumulated in the control section 4a. The "display method" is such in which the displaying order of when displaying the extracted measurement information in the list part 10d-1a is defined.

Whether or not the display condition button has been pushed (whether or not display condition is selected) is determined by the control section 4a in step S27 of the flowchart shown in FIG. 15. When the display condition button has not been pushed, the process returns to step S27. When the user selects an arbitrary display condition in the display condition dialogue 20, the extracting part 411 of the control section 4a acquires the display condition (extracting information) selected from the database 415, searches the measurement information database 410 according to the extracting condition of the selected display condition (extracting information), and extracts the measurement information that matches the extracting condition in step S28. For instance, if "current day" is selected as the display condition, the data items on the measurement date and time in the measurement information are searched, and the measurement information for the current day are extracted. The extracted measurement information are provided to the display part 412 and displayed in a list on the list part 10d-1a according to the order of the display method in the selected display condition in step S29.

Among each display item of the displayed measurement information, the measurement result (measurement value) is displayed for the measured display items, and a "check" mark is displayed for the non-measured or in-measurement display items regarding the display items of the measurement result (see FIG. 4).

As shown in FIG. 4, when the display condition is selected, the display condition name ("current day" in FIG. 4) is displayed on the title bar 10a of the screen 10. The name of the selected display condition (extracting information) is displayed with the display of the measurement information, so that the user can easily check what display condition (extracting information) is currently being displayed even if a plurality of display conditions (extracting information) is present.

In step S30 of the flowchart shown in FIG. 15, whether or not the display instruction of the display condition setting dialogue is made is judged by the control section 4a, where the display condition setting dialogue is displayed in step S31 if the display instruction of the display condition setting dialogue is made. If the display instruction of the display condition setting dialogue is not made, the process proceeds to step S35. The display condition setting dialogue is displayed by first displaying the customize dialogue and pushing the "display condition setting" button in the "display condition" tab.

The customize dialogue will be described in detail below.

When the "customize" button P3-b is selected in the screen 10 of FIG. 4, the customization of the display condition etc. of the list part 10d-1a is performed. That is, the user is able to create a new customized display condition 22 or edit the already registered display conditions 21, 22. The user may also set the display items of the measurement information displayed in the list part 10d-1a.

Figure 7:
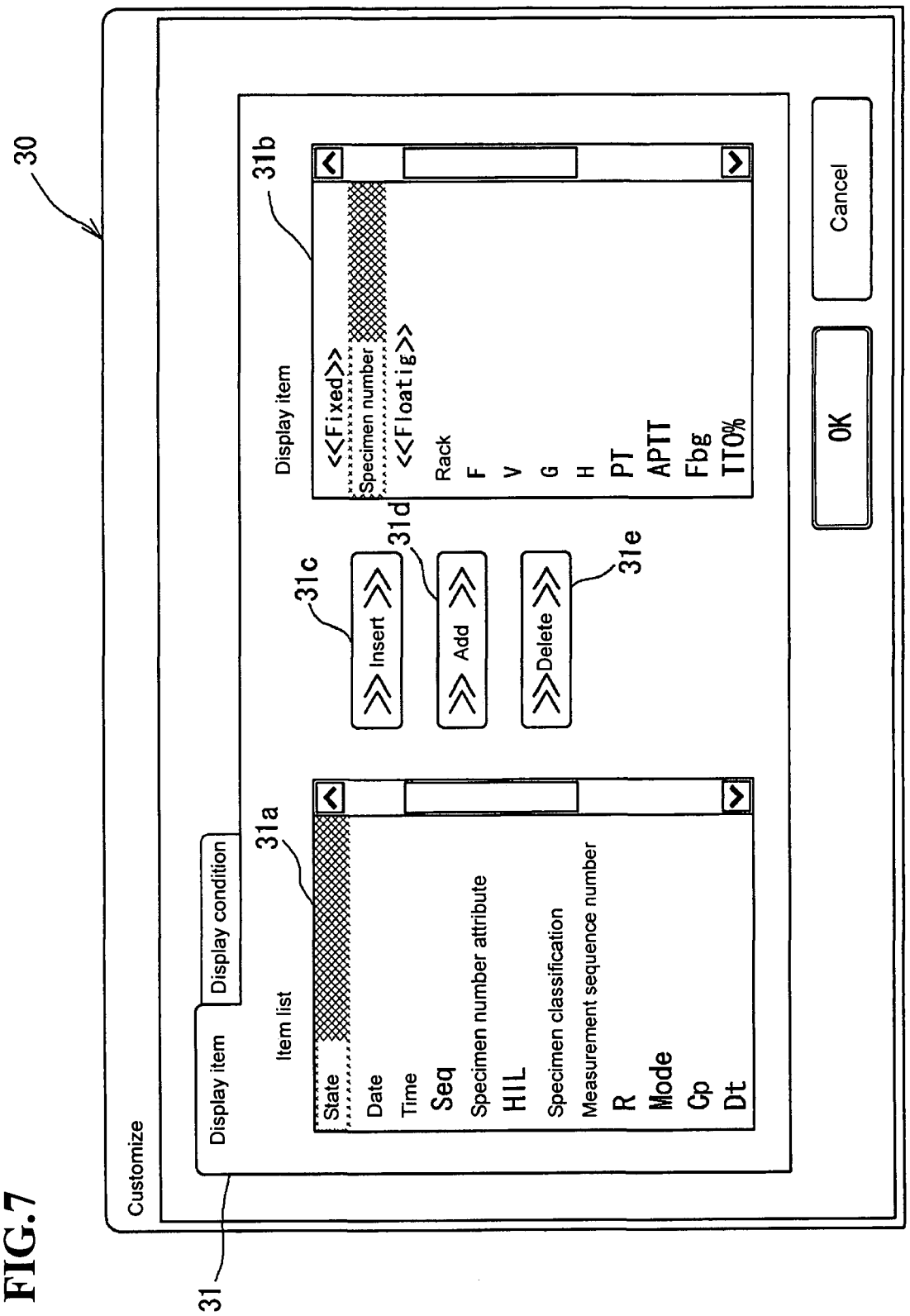
FIG. 7 is a view showing a display item tab of a customize dialogue.
Figure 8:
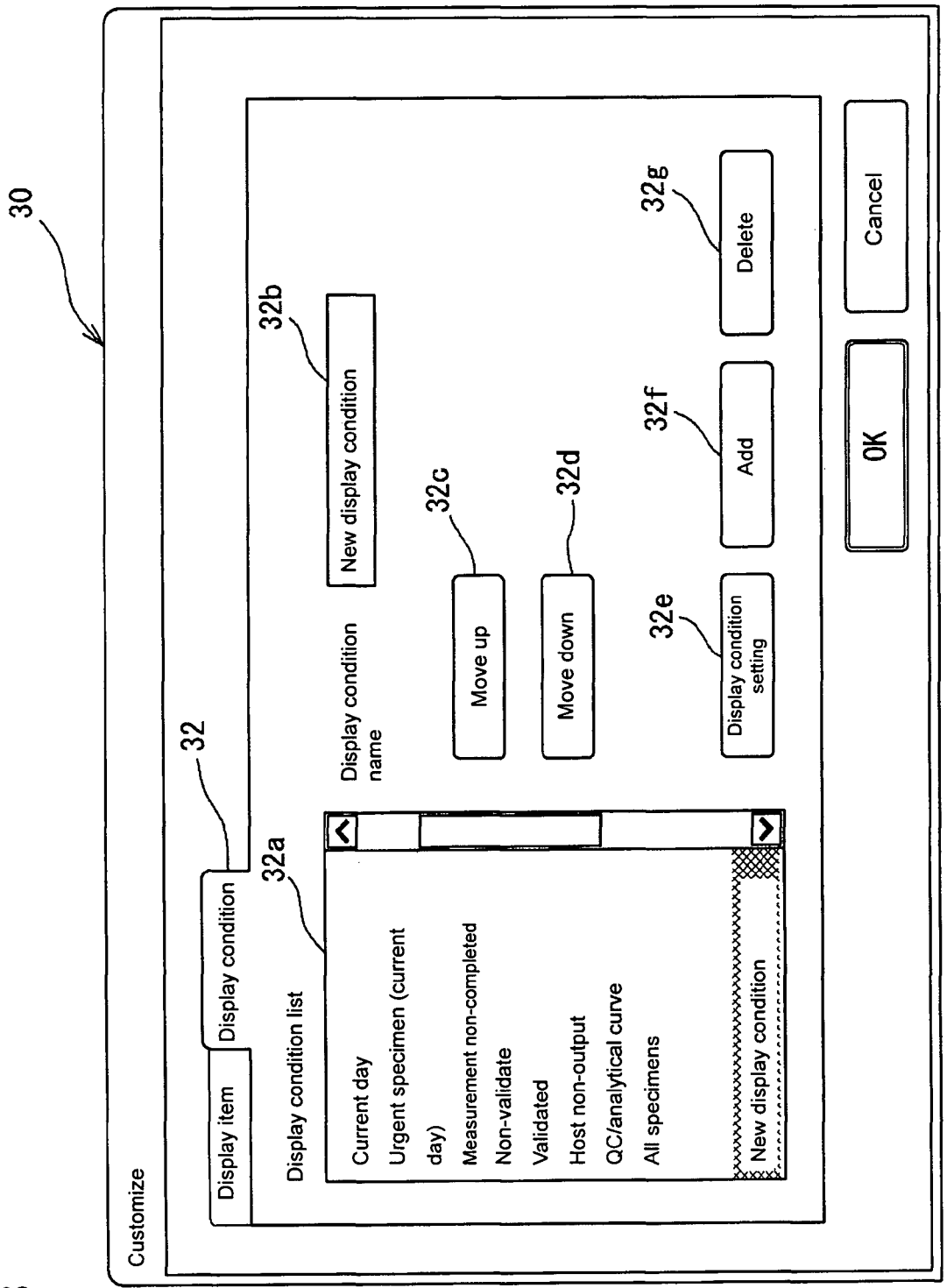
FIG. 8 is a view showing a display condition tab of the customize dialogue.

When the "customize" button P3-b is pushed, the customize dialogue (customize screen; customize section 413) 30 shown in FIGS. 7 and 8 is displayed. However, the customize dialogue will not be displayed if the user not having authority pushes the "customize" button P3-b, and instead, a warning dialogue will be displayed. The authority for customization is determined by a login account to the application program 404a. For instance, when logged in under the authority of the night operator, customization of the display cannot be performed. Therefore, change/addition of the display condition etc. by the unauthorized person is prevented.

The customize dialogue 30 includes a "display item" setting tab (display item setting part 413a) 31 as shown in FIG. 7, and a "display condition" setting tab (display condition setting part 413b) as shown in FIG. 8.

In the display item setting tab 31 of FIG. 7, the selection of the display items of the measurement information displayed in the list part 10d-1a and the setting of the order thereof are performed. The display item setting tab 31 includes an item list part 31a for indicating a list of options of the items of the measurement information displayable on the list part 10d-1a, and a display item part 31b or a field for setting the display item displayed on the list part 10d-1a. In the <<Fixed>> item of the display item part 31b, the item that is not erased from the display even when the display of the list part 10d-1a is horizontal scrolled by the button part 10d-1b is set, and the horizontal scrolled item is set in the <<Floating>> item.

The display item setting tab 31 includes an insertion button 31c for inserting the item being selected with the cursor of the item list part 31a to a cursor position of the display item part 31b, an addition button 31d for adding the item being selected with the cursor of the item list part 31a to the undermost row of the display item part 31b, and a delete button 31e for deleting the item being selected with the display item part 31c.

The items displayed in the list part 10d-1a can be freely set by the user by setting the items desired to be displayed in the list part 10d-1a in the display item part 31 through the operation of the buttons 31c, 31d, and 31e. The set display items are stored in the display information database of the control section 4a. After setting the display items, the set display item out of each data item of the measurement information extracted by the selected display condition is displayed on the list part 10d-1a.

The setting of the display item is effective in common to a plurality of display conditions, and the same display item is displayed irrespective of which display condition is selected, and thus unity of the display can be maintained. The display item may be individually set for each display condition.

In the display condition setting tab 32 of FIG. 8, the setting of the display condition (new document, delete, edit) is performed. The display condition setting tab 32 includes a display condition list part 32a for displaying a list of the display conditions registered in the display information database 414 of the control section 4a.

Furthermore, the display condition setting tab 32 includes a display condition name display part 32b for displaying the name of the display condition being selected in the display condition list part 32a, a "move up" button 32c for moving up by one the display condition selected in the display condition list part 32a, a "move down" button 32d for moving down by one the display condition selected in the display condition list part 32a, a "display condition setting" button 32e for displaying the display condition setting dialogue for performing change (edit) of the display condition being selected in the display condition list part 32a, an "add" button 32f for adding a new display condition to the display condition list part 32a, and a "delete" button 32g for deleting the display condition being selected in the display condition list part 32a.

When adding the new display condition, the user first selects the "add" button 32f. The additional display condition is then generated under the name "new display condition" as shown in FIG. 8. When setting (changing) the name of the display condition is desired, the user only needs to input the name to the display condition name display part 32b.

Figure 11:
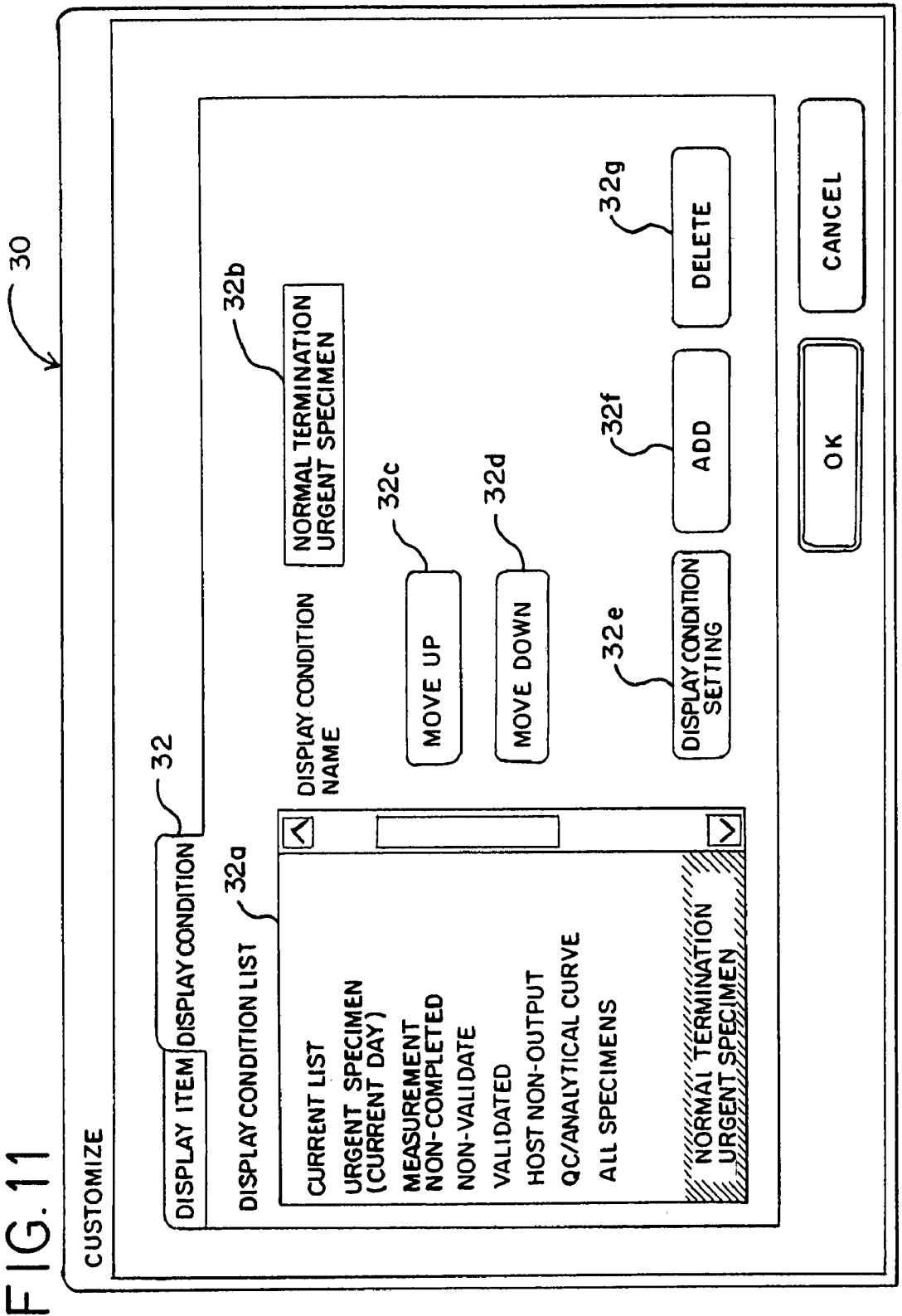
FIG. 11 is a view showing a display condition tab of the customize dialogue when giving a new display condition name.

For instance, as shown in FIG. 11, the user can change the name "new display condition" displayed in the display condition name display part 32b to "normal termination urgent specimen" using the keyboard 4c.

Figure 9:
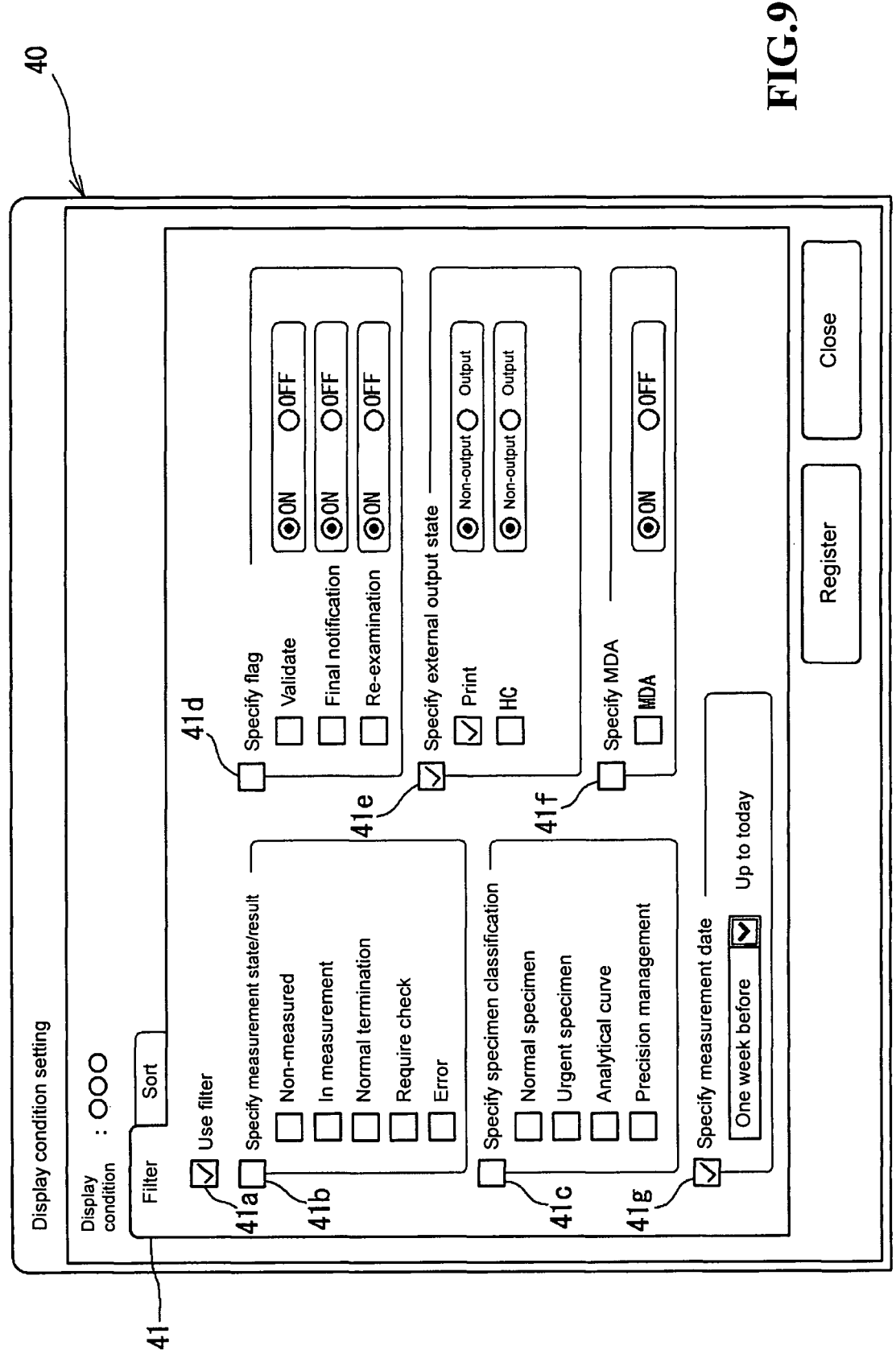
FIG. 9 is a view showing a filter tab of a display condition setting dialogue.
Figure 10:
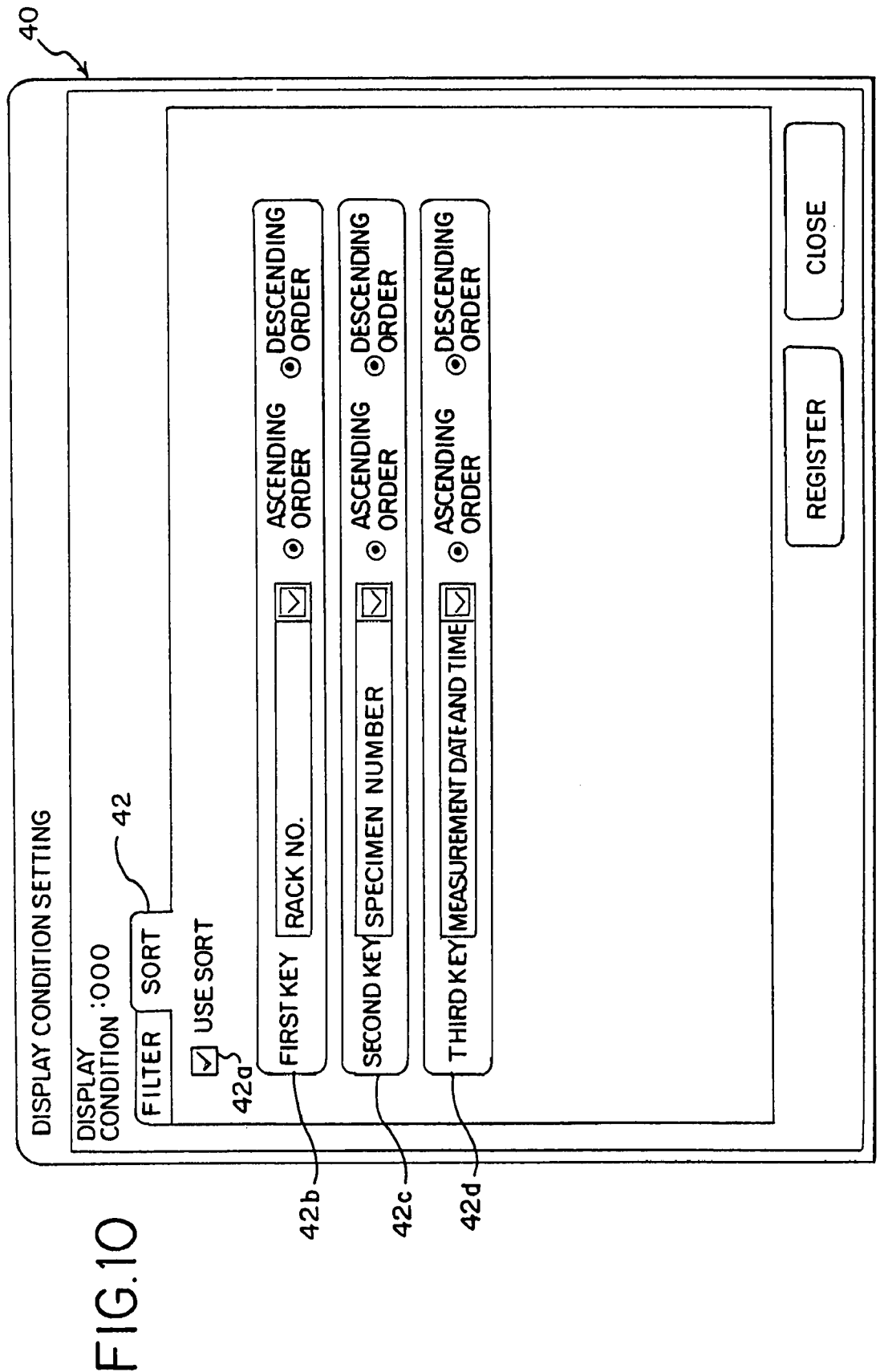
FIG. 10 is a view showing a sort tab of the display condition setting dialogue.

When setting the content of the display condition, the "display condition setting" button 32e is selected, and the display condition setting dialogue (display condition setting screen) 40 shown in FIGS. 9 and 10 is displayed.

The display condition setting dialogue 40 includes a filter tab (extracting information setting screen; extracting condition setting means) 41 shown in FIG. 9, and a sort tab (display method (display order) setting screen; display method (display order) setting unit) shown in FIG. 10.

The acceptance of the setting in step S32 is executed by selecting a check box described below.

The filter tab 41 shown in FIG. 9 includes a "use filter" check box 41a, a "specify measurement state/result" check box 41b, a "specify specimen classification" check box 41c, a "specify flag" check box 41d, a "specify external output state" check box 41e, a "MDA measurement" check box 41f, and a "specify measurement date" check box 41g.

The "use filter" check box 41a is provided to select whether or not to use the extracting conditions (filter conditions) set in the filter tab 41.

The "specify measurement state/result" check box 41b is provided to select whether or not to perform search on the "measurement state" out of the data items of the measurement information. When the check box 41b is checked, the measurement information can be extracted for every measurement state by checking the check box of each state of "non-measured", "in-measurement", "normal termination", "require check", and "error". A plurality of measurement states can be checked.

In the present embodiment, the "measurement state" can be set as the extracting condition, and thus the progress of the measurement (non-measured, in-measurement, measurement terminated) can be set as the extracting condition. Therefore, the "non-measured" and the "in-measurement" check boxes are checked when desiring to extract those in which the measurement are not completed, and the "normal termination", "require check" and "error" check boxes are checked when desiring to extract those in which the measurement are terminated.

The "specify specimen classification" check box 41c is provided to select whether or not to perform a search on the "specimen classification" out of the data items of the measurement information. When the check box 41c is checked, the measurement information can be extracted for every type of specimen by checking the check box of each classification of "normal specimen", "urgent specimen", "analytical curve", and "precision management". A plurality of specimen classifications can be checked.

The "specify flag" check box 41d is provided to select whether or not to perform the search on "validate flag", "final flag", and "re-examination flag" out of the data items of the measurement information. When the check box 41d is checked, the measurement information can be extracted according to the state (ON/OFF) of each flag by checking the check box of each flag of "validate", "final notification", and "re-examination". A plurality of flags can be checked.

The validate flag indicates whether or not the measurement result is validated (validate state). The final flag is indicated as being the final measurement information when a plurality of measurement information (measurement results) exists for one specimen. If only one measurement information exists for one specimen and re-measurement is not performed, the relevant measurement information is assumed as the final measurement information. The re-examination flag is indicated as being the re-measured measurement information.

In the present embodiment, the state of the measurement result (presence of validate, whether final or not, whether re-measurement or not) can be set as the extracting condition of the measurement information, and thus the measurement information can be extracted according to the state of the measurement result.

The "specify external output state" check box 41e is provided to select whether or not to perform a search on a "printer output state flag" and a "host output state flag" out of the data items of the measurement information. When the check box 41e is checked, the measurement information can be extracted according to the state (ON/OFF) of each flag by checking the check box of each flag of "print", "HC" (abbreviation for Host Computer). A plurality of flags can be checked.

Here, the "print output state flag" indicates whether or not the measurement information is output to the printer, that is, whether or not printed. The "host output state flag" indicates whether or not the measurement information is output to the host computer 100.

In the present embodiment, the measurement information can be extracted according to the necessity of output since the necessity of output of the measurement information can be set as the extracting information.

The "specify MDA" check box 41f is provided to select whether or not to perform a search on a "MDA flag" out of the data items of the measurement information. The measurement information can be extracted according to the state (ON/OFF) of the "MDA flag" by checking the check box 41f and checking the "MDA" check box.

The "MDA flag" indicates the necessity of MDA (Multi Dilution Analysis). The MDA refers to performing a plurality of measurements with different dilution scale factors with respect to the same specimen.

The "specify measurement date" check box 41g is provided to select whether or not to perform a search on a "measurement date and time" out of the data items of the measurement information. The measurement information can be extracted according to the measurement date (measurement period) by checking the check box 41g, and setting the measurement date of the extracted measurement information.

When the user appropriately selects the extracting conditions described above, the extracting information (display condition) consisting of a combination of various extracting conditions can be set in the filter tab 41. When the user selects the registration button with the extracting conditions selected, the extracting information is stored and registered in the hard disc 401d. Furthermore, a new button corresponding to such registered extracting information is added to the display condition dialogue 20.

When the display condition setting dialogue described above is displayed, the setting of the extraction conditions as described above from the user is accepted by the control section 4a (step S32), and judgment is made on whether or not the registration button is selected (step S33). If the setting is not accepted or if the setting is not completed in step S33, the process returns to step S32.

Figure 12:
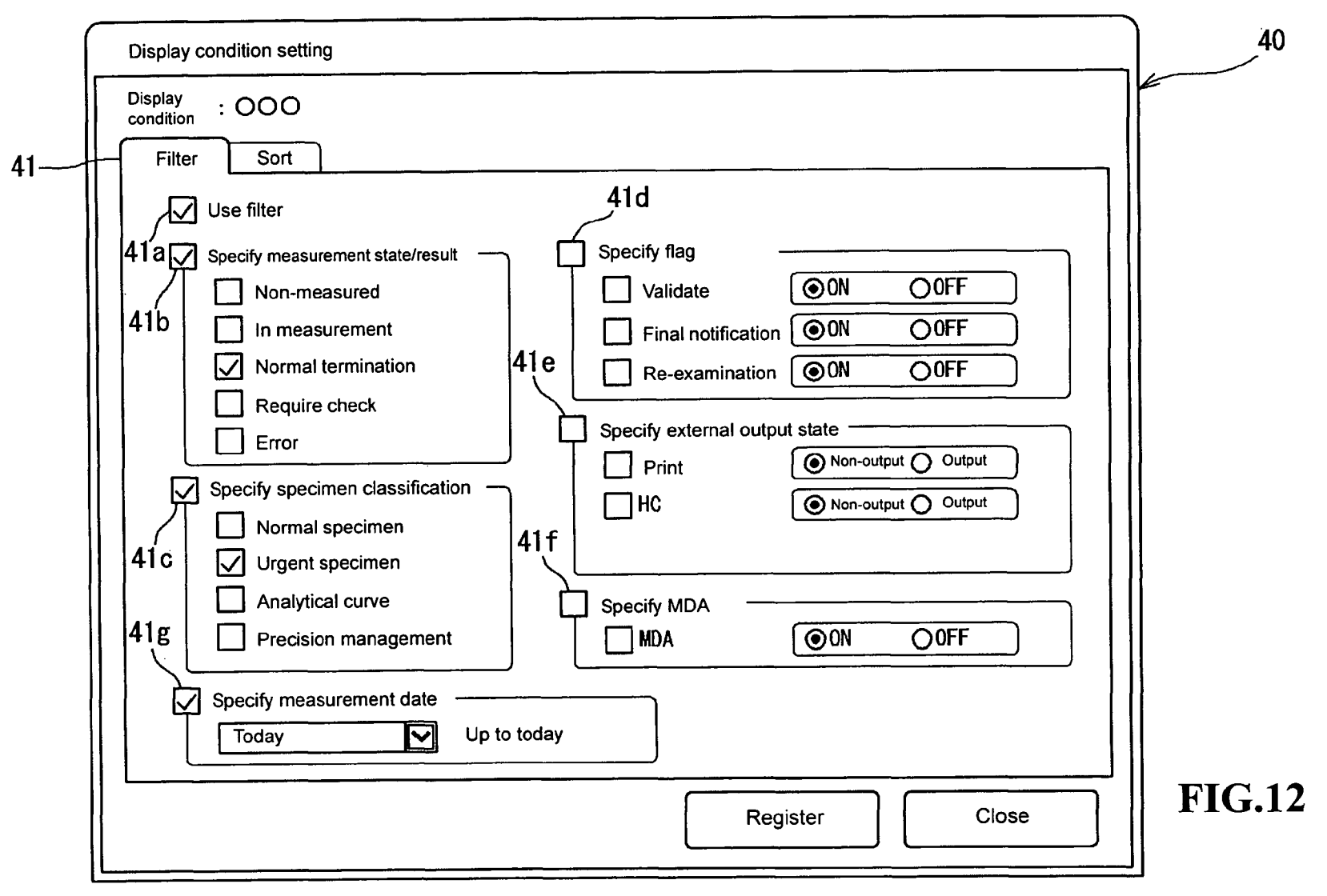

For instance, an example in which the display condition of "normal termination urgent specimen" is set as the new display condition is shown in FIG. 12. In the display condition dialogue of the "normal termination urgent specimen" shown in FIG. 12, the "use filter" check box 41a is checked, the "specify measurement state/result" check box 41b is checked and furthermore the normal termination is checked, the "specify specimen classification" check box 41c is checked and furthermore the urgent specimen is checked, and the "specify measurement date" check box 41g is checked and furthermore "today" is checked. The "normal termination urgent specimen" in which the display conditions of the normally terminated specimen in the urgent specimen measured today are shown can be set.

When the selection of the registration button is accepted by the control section 4a in step S33 of the flowchart shown in FIG. 15, the display condition is registered in step S34. The registered display condition is added as a new display condition button in the display condition dialogue 20. Specifically, the display condition of the "normal termination urgent specimen" of the display condition list part 32a of the customize dialogue 30 shown in FIG. 11 is registered by pushing the "register" button of the display condition dialogue 40 of the "normal termination urgent specimen" shown in FIG. 12, and the customize dialogue 30 is closed by pushing the "OK" button of the customize dialogue 30. Accordingly, the "normal termination urgent specimen" showing the display condition of the specimen normally terminated in the urgent specimen measured today is set as the "normal termination urgent specimen" button 20i of the display condition dialogue 20 shown in FIG. 6. Thus, when searching for the specimen desired by the user, the desired specimen can be easily searched by simply pushing the button linked with the registered display condition by selecting and registering the display condition of the desired specimen in advance.

The display conditions used by the user tend to be more or less constant. That is, most of the users repeatedly use the specific display conditions. It is convenient to set and register the conditions having high usage frequency.

The sort tab 42 shown in FIG. 10 is provided to set to the conditions for performing the sort of the measurement information extracted in the extracting conditions set in the filter tab 41, and includes "use sort" check box 42a, a "first key" setting part 42b, a "second key" setting part 42c, and a "third key" setting part 42d for sorting.

The "use sort" check box 42a is provided to select whether or not to use the display method (display order, sort order) set in the sort tab 42. If the check box 42a is not checked, the extracted measurement information is displayed in ascending order of the measurement date and time.

The "first key" setting part 42b is provided to select the first key of sorting, and selects the item ("rack number" in FIG. 10) that is to become the key in sorting out of the data items of the measurement information, and sets the lining order (ascending order or descending order) of the measurement information with the relevant key.

The "second key" setting part 42c and the "third key" setting part 42d can also perform the setting similar to the "first key" setting part 42b. The first key is applied in preference to the second key and the third key, and the second key is applied in preference to the third key.

In the sort tab 42, the measurement information can be displayed in the order easily viewable by the user since the display order (display method) of the measurement information can be appropriately set by the user.

Furthermore, since both the extracting information and the display method can be set in one display condition, the display method can be set according to the measurement information to be extracted, and the display method can be easily changed according to the extracting condition.

Furthermore, since the extracting information set in the filter tab 42 and the display method set in the sort tab 42 are integrated as "display condition", both the extracting information and the display method can be selected by simply selecting the display condition in the display condition dialogue 20 of FIG. 6, whereby the operation is facilitated. In other words, in the present embodiment, the extracting information set in the filter tab 42 and the display method set in the sort tab 42 do not need to be separately selected, and collective selection can be made.

Thereafter, when the user selects shut down from the tool bar 10c (FIG. 4) of the screen 10 displayed on the display device 4b of the control device 4 in step S35 of the flowchart shown in FIG. 15, the shut down signal is transmitted in step S36 to the control section of the measurement mechanism unit 2 by the control section 4a in step S16, the shut down of the control device 4 and the measurement mechanism unit 2 is performed, and the process is terminated. If shut down is not selected in step S35, the process returns to step S25.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A clinical sample measurement device comprising:
  a measurement unit configured for measuring a clinical sample; and
  a computer system connected to the measurement unit, comprising:
    a display section; and
    a storage part under control of a processor, the storage part storing:
      a measurement non-completed sample extracting condition indicating that measurement information of clinical samples, whose measurements have not been completed, is extracted, wherein the measurement information comprises state information indicating whether measurement of the clinical samples has been completed; and
      instructions enabling the processor to carry out operations, comprising:
        accepting a customize condition indicating that measurement information, corresponding to a condition set by a user of the clinical sample measurement device, is extracted;
        storing the accepted customize condition;
        storing the measurement information of clinical samples;
        updating the measurement information when measurements have been completed, such that the state information indicates measurements have been completed;
        accepting a selection of the measurement non-completed sample extracting condition or the customize condition;
        extracting measurement information indicating measurements have not been completed from the storage part when the measurement non-completed sample extracting condition has been selected; and
        displaying the extracted measurement information on the display part.

2. The clinical sample measurement device according to claim 1, wherein the operations further comprise:
  displaying a first button for selecting the measurement non-completed sample extracting condition and a second button for selecting the customize condition;
    wherein selection of the measurement non-completed sample extracting condition and the customize condition is accepted via the buttons.

3. The clinical sample measurement device according to claim 1, wherein the operations further comprise:
  displaying a customize condition setting screen for inputting the customize condition;
    wherein the customize condition is accepted via the customize condition setting screen.

4. The clinical sample measurement device according to claim 1, wherein the customize condition comprises a combination of extracting conditions.

5. The clinical sample measurement device according to claim 1, wherein the measurement information comprises a date of measurement, and wherein the storage part further stores an extracting condition to extract the measurement information based on the date of measurement.

6. The clinical sample measurement device according to claim 1, wherein the measurement information comprises validation information indicating whether the clinical samples have been validated, and wherein the storage part further stores an extracting condition to extract the measurement information based on whether the clinical samples have been validated.

7. A measurement information of clinical samples display method comprising:
  accepting a customize condition indicating that measurement information, corresponding to a condition set by a user of the clinical sample measurement device, is extracted;
  storing the accepted customize condition;
  storing measurement information of clinical samples, the measurement information comprising state information indicating whether measurement of the clinical samples has been completed;
  updating the measurement information when measurements have been completed, such that the state information indicates measurements have been completed;
  accepting a selection of a measurement non-completed sample extracting condition or the customize condition, the measurement non-completed sample extracting condition indicating that measurement information of clinical samples, whose measurements have not been completed, is extracted;

extracting measurement information indicating measurements have not been completed when the measurement non-completed sample extracting condition has been selected; and displaying the extracted measurement information.

8. The measurement information of clinical samples display method according to claim 7, further comprising:

displaying a first button for selecting the measurement non-completed sample extracting condition and a second button for selecting the customize condition;

wherein the selection of the measurement non-completed sample extracting condition and the customize condition is accepted via the buttons.

9. The measurement information of clinical samples display method according to claim 7, further comprising:

displaying a customize condition setting screen for inputting the customize condition;

wherein the customize condition is accepted via the customize condition setting screen.

10. The measurement information of clinical samples display method according to claim 7, wherein the customize condition comprises a combination of extracting conditions.

11. A computer system configured to display measurement information of clinical samples, comprising:

a display section;

a storage part under control of a processor, the storage part storing:

a measurement non-completed sample extracting condition indicating that measurement information of clinical samples, whose measurements have not been completed, is extracted, wherein the measurement information comprises state information indicating whether measurement of the clinical samples has been completed; and instructions enabling the processor to carry out operations, comprising:

accepting a customize condition Indicating that measurement information, corresponding to a condition set by a user of the clinical sample measurement device, is extracted;

storing the accepted customize condition;

storing the measurement information of clinical samples;

updating, when measurements have been completed, the measurement information such that the state information indicates measurements have been completed;

accepting a selection of the measurement non-completed sample extracting condition or the customize condition;

extracting measurement information indicating measurements have not been completed from the storage part when the measurement non-completed sample extracting condition has been selected; and displaying the extracted measurement information on the display part.

12. The computer system according to claim 11, wherein:

the operations further comprise displaying a first button for selecting the measurement non-completed sample extracting condition and a second button for selecting the customize condition; and selection of the measurement non-completed sample extracting condition and the customize condition is accepted via the buttons.

13. The computer system according to claim 11, wherein:

the operations further comprise displaying a customize condition setting screen for inputting the customize condition; and the customize condition is accepted via the customize condition setting screen.

14. The computer system according to claim 11, wherein the customize condition comprises a combination of extracting conditions.

15. The computer system according to claim 11, wherein:

the measurement information comprises a date of measurement; and the storage part further stores an extracting condition to extract the measurement information based on the date of measurement.

16. The computer system according to claim 11, wherein:

the measurement information comprises validation information indicating whether the clinical samples have been validated; and the storage part further stores an extracting condition to extract the measurement information based on whether the clinical samples have been validated.

* * * * *